(12) United States Patent
Laughery et al.

(10) Patent No.: US 8,521,538 B2
(45) Date of Patent: Aug. 27, 2013

(54) VOICE ASSISTANT SYSTEM FOR DETERMINING ACTIVITY INFORMATION

(75) Inventors: Michael Laughery, Monroeville, PA (US); Bonnie Praksti, Monroeville, PA (US); David M. Findlay, Freeport, PA (US); James E. Shearon, Pittsburgh, PA (US)

(73) Assignee: Vocollect Healthcare Systems, Inc., Pittsburgh, PA (US)

( * ) Notice: Subject to any disclaimer, the term of this patent is extended or adjusted under 35 U.S.C. 154(b) by 247 days.

(21) Appl. No.: 12/879,704

(22) Filed: Sep. 10, 2010

(65) Prior Publication Data

US 2011/0040564 A1    Feb. 17, 2011

Related U.S. Application Data

(63) Continuation-in-part of application No. 12/536,696, filed on Aug. 6, 2009, now Pat. No. 8,255,225.

(60) Provisional application No. 61/087,082, filed on Aug. 7, 2008.

(51) Int. Cl.
*G10L 21/00* (2006.01)
(52) U.S. Cl.
USPC ............ 704/275; 704/231; 704/256; 704/270
(58) Field of Classification Search
USPC .............. 704/231, 258, 270–271; 601/23–45
See application file for complete search history.

(56) References Cited

U.S. PATENT DOCUMENTS 4,213,253 A     7/1980   Gudelis
4,629,015 A  *  12/1986  Fried et al. ................. 177/25.19
(Continued)

FOREIGN PATENT DOCUMENTS

| EP | 1791053 | 5/2007 |
| WO | WO9525326 | 9/1995 |
| WO | WO02096126 | 11/2002 |
| WO | WO2005043303 | 5/2005 |

OTHER PUBLICATIONS

Forty-Seven-page "The Digital Consumer Technology Handbook", A Comprehensive Guide to Devices, Standards, Future Directions, and Programmable Logic Solutions; by Amit Dhir, Xilinx, Inc. dated Feb. 27, 2004.

*Primary Examiner* — Douglas Godbold
(74) *Attorney, Agent, or Firm* — Wood, Herron & Evans, LLP

(57) ABSTRACT

A system and method of assisting a care provider in the documentation of self-performance and support information for a resident or person includes a speech dialog with a care provider that uses the generation of speech to play to the care provider and the capture of speech spoken by a care provider. The speech dialog provides assistance to the care provider in providing care for a person according to a care plan for the person. The care plan includes one or more activities requiring a level of performance by the person. For the activity, speech inquiries are provided to the care provider, through the speech dialog, regarding performance of the activity by the person and regarding care provider assistance in the performance of the activity by the person. Speech input is captured from the care provider that is responsive to the speech inquiries. A code is then determined from the speech input and the code indicates the self-performance of the person and support information for a care provider for the activity.

17 Claims, 11 Drawing Sheets

(56) References Cited

U.S. PATENT DOCUMENTS

| | | |
|---|---|---|
| 5,077,666 A | 12/1991 | Brimm et al. |
| 5,536,084 A | 7/1996 | Curtis et al. |
| 5,754,111 A | 5/1998 | Garcia |
| 5,822,544 A * | 10/1998 | Chaco et al. ............... 705/2 |
| 5,838,223 A * | 11/1998 | Gallant et al. ........ 340/286.07 |
| 5,853,377 A * | 12/1998 | Madsen et al. ............. 600/587 |
| 5,857,939 A * | 1/1999 | Kaufman ..................... 482/8 |
| 5,986,568 A * | 11/1999 | Suzuki et al. ................ 340/9.1 |
| 6,057,758 A | 5/2000 | Dempsey et al. |
| 6,292,783 B1 | 9/2001 | Rohler et al. |
| 6,296,595 B1 * | 10/2001 | Stark et al. ..................... 482/91 |
| 6,591,242 B1 | 7/2003 | Karp et al. |
| 6,714,913 B2 * | 3/2004 | Brandt et al. ................... 705/2 |
| 6,720,864 B1 | 4/2004 | Wong et al. |
| 6,747,556 B2 * | 6/2004 | Medema et al. ........ 340/539.12 |
| 6,772,454 B1 | 8/2004 | Barry |
| 6,849,045 B2 * | 2/2005 | Iliff ............................. 600/300 |
| 6,872,080 B2 * | 3/2005 | Pastrick et al. .............. 434/262 |
| 6,890,273 B1 | 5/2005 | Perez |
| 7,065,381 B2 | 6/2006 | Jenkins |
| 7,228,429 B2 | 6/2007 | Monroe |
| 7,283,845 B2 | 10/2007 | De Bast |
| 7,287,031 B1 | 10/2007 | Karpf et al. |
| 7,574,370 B2 | 8/2009 | Mayaud |
| 7,664,657 B1 * | 2/2010 | Letzt et al. ..................... 705/2 |
| 8,257,284 B2 * | 9/2012 | Gruben et al. ............... 601/33 |
| 2002/0004729 A1 | 1/2002 | Zak et al. |
| 2002/0146096 A1 | 10/2002 | Agarwal et al. |
| 2003/0182117 A1 * | 9/2003 | Monchi et al. ............... 704/237 |
| 2003/0208357 A1 * | 11/2003 | Hammond ..................... 704/270 |
| 2004/0220686 A1 | 11/2004 | Cass |
| 2004/0243027 A1 * | 12/2004 | Hook ........................... 601/33 |
| 2006/0200354 A1 * | 9/2006 | Ito et al. ..................... 704/275 |
| 2006/0253281 A1 * | 11/2006 | Letzt et al. ................. 704/231 |
| 2007/0073168 A1 * | 3/2007 | Zhang et al. ................ 600/483 |
| 2007/0219806 A1 * | 9/2007 | Yamaki ....................... 704/275 |
| 2007/0221138 A1 | 9/2007 | Mainini et al. |
| 2008/0021709 A1 * | 1/2008 | Greer ........................... 704/258 |
| 2008/0072847 A1 | 3/2008 | Liao |
| 2008/0082338 A1 * | 4/2008 | O'Neil et al. ............... 704/275 |
| 2008/0161733 A1 * | 7/2008 | Einav et al. ................. 601/34 |
| 2009/0069156 A1 * | 3/2009 | Kurunmaki et al. ............ 482/9 |
| 2009/0171667 A1 * | 7/2009 | Rivera ........................... 704/275 |
| 2009/0177477 A1 * | 7/2009 | Nenov et al. ................ 704/275 |
| 2009/0216534 A1 | 8/2009 | Somasundaram |
| 2010/0026817 A1 * | 2/2010 | Ryan et al. ............... 348/207.11 |
| 2010/0036667 A1 | 2/2010 | Byford et al. |
| 2010/0052871 A1 | 3/2010 | Somasundaram et al. |
| 2010/0286490 A1 * | 11/2010 | Koverzin ..................... 600/301 |

* cited by examiner

25

Brown, John
CNA, Meadowlark Lemon Estates
logout

[People Search]

Jane Anne Doe
postion: chair
May 13, 3:53 PM

Site
Unit
Residents
Staff
Reports
About

You are here . . . > Residents > Jane Doe > Toileting

I want to... ▶

Toileting

Physical Functioning - Bowel
SELECTED: Continence bowel: Usually continent, Level of support bowel: One person physical; Self-performance bowel: Limited assistance.

Self-performance: [Limited assistance ▶]
Level of support provided: [One person physical assist ▶]
Continence: [Usually continent ▶]

Physical Functioning - Bladder
SELECTED: Continence bladder: Occasionally incontinent; Level of support bladder: One person physical assist; Self-performance bladder: Limited assistance.

Self-performance: [Limited assistance ▶]
Level of support provided: [One person physical assist ▶]
Continence: [Occasionally incontinent ▶]

Cautions
SELECTED: Do not leave unattended in bathroom; High risk for falls.

☑ Do not leave unattended in bathroom
☑ High risk for falls
☐ Assistance needed for toileting transfer
☐ Notify nurse if dressing soiled or removed

Monitoring
SELECTED: Scheduled toileting.

Set up a schedule:
○ None
◉ Scheduled toileting
   X 12:00 PM
   X 2:00 PM
   [Select time... ▶] [AM/PM... ▶] Add another?
○ Bladder training program

Check and change briefs

Starts: 🗓 [Select time... ▶] [AM/PM... ▶]
Repeats: [Select time... ▶] [Select time... ▶]
Ends: ◉ Never
    ○ Until

FIG. 2A

☐ Record urine output in ccs
Special Equipment
*No summary found.*
☐ Uses bedside commode or urinal
Uses bedpan: [Does not use bedpan ▶]
Uses catheter: [Does not use catheter ▶]
Briefs
*SELECTED: uses standard briefs.*
○ None
◉ Uses standard briefs  [Medium ▶]
○ Uses special briefs
☐ Family suppplies incontinense product
Incontinence
*SELECTED: Apply barrier cream to perineal area; Pericare after incontinent episode.*
☑ Uses bedside commode or urinal
[Apply barrier cream to perineal area. ▶]
Ostomy Care
*No summary found.*
☑ Has colostomy bag
☑ Independent with colostome care
☐ Has urostomy bag
☐ Independent with ostomy care
☐ Notify nurse when care required
Custom Notes
*No custom notes.*
Custom Notes
None available.
Add New Note

*Notes longer than 1000 characters will be truncated.*
Expires:
◉ Never
○ Date: [      ] 🗓

[ Save my changes ]  [ Do not save my changes ]

FIG. 2B

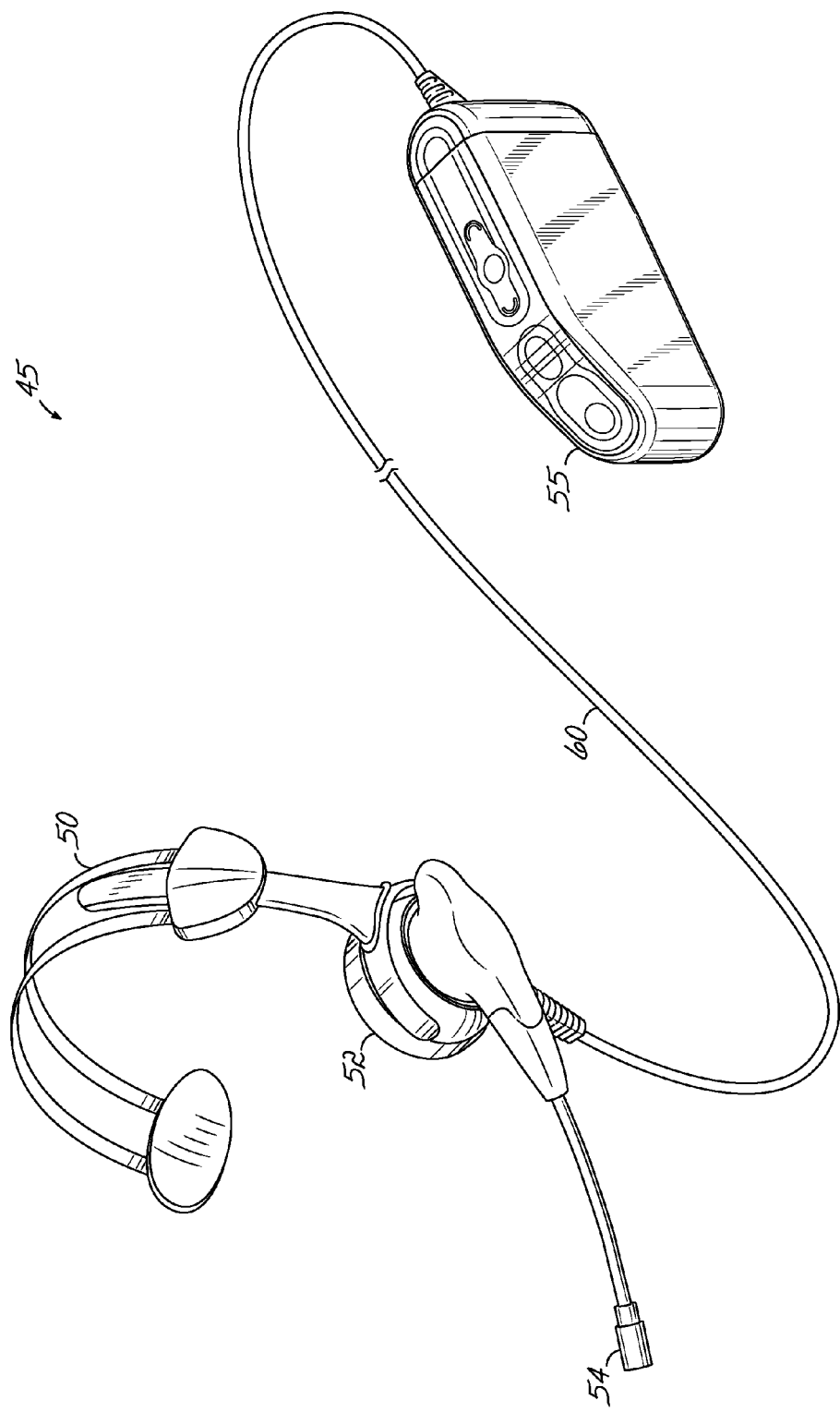

VOICE ASSISTANT SYSTEM FOR DETERMINING ACTIVITY INFORMATION

RELATED APPLICATIONS

This Application is a continuation-in-part of U.S. Non-Provisional patent application Ser. No. 12/536,696, entitled "VOICE ASSISTANT SYSTEM", filed Aug. 6, 2009, now U.S. Pat. No. 8,255,225 which Application claims priority to U.S. Provisional Patent Application No. 61/087,082, entitled "VOICE ASSISTANT SYSTEM", filed Aug. 7, 2008, which Applications are incorporated herein by reference in their entireties.

FIELD OF THE INVENTION

This invention generally relates to the use of speech or voice technology in a work environment to facilitate a variety of work tasks.

BACKGROUND OF THE INVENTION

Speech or voice technology, in the form of speech recognition, is used in a variety of different environments to facilitate the completion of work or various tasks. One example of a specific use for a voice-directed system is the direction of a worker to perform various tasks and to collect data associated with the task execution.

In a typical voice-directed work system, the worker wears a mobile computer having voice or speech capabilities. The computer is worn on the body of a user, such as at their waist, and a headset device connects to the mobile computer, such as with a cable or possibly in a wireless fashion. In another embodiment, the mobile computer might be implemented directly in the headset. The headset includes one or more speakers for playing voice instructions and other audio that are generated or synthesized by the mobile computer to direct the work of the user and to confirm the spoken words of the user. The headset also has a microphone for capturing the speech of the user to determine the commands spoken by the user and to allow the entry of data using the user's speech and speech recognition. Through the headset and speech recognition and text-to-speech capabilities of the mobile computer, workers are able to receive voice instructions or questions about their tasks, to receive information about their tasks, to ask and answer questions, to report the progress of their tasks, and to report various working conditions, for example.

The mobile computers provide a significant efficiency in the performance of a user's tasks. Specifically, using such mobile computers, the work is done virtually hands-free without equipment to juggle or paperwork to carry around. The mobile and/or wearable computers allow the workers or other users that wear or use them to maintain mobility at a worksite, while providing the users with desirable computing and data-processing functions. Generally, such mobile computers often provide a wireless communication link to a larger, more centralized computer system that directs the work activities of a user within a system and processes any user speech inputs, such as collected data, in order to facilitate the work. An overall integrated system may utilize a central system that runs a variety of programs, such as a program for directing a plurality of mobile computers and their users in their day-to-day tasks. The users perform manual tasks and enter data according to voice instructions and information they receive from the central system, via the mobile computers.

One process is generally referred to as voice-directed work as the user takes specific direction from the central system and their computer like they might take direction from a manager or supervisor or from reading a work order or to-do list. However, voice-directed systems may be overly structured for some users and for some work environments. Various work environments require that the worker know what they are doing in any particular task, and thus they do not have to be told how to specifically perform a particular task or what order to handle multiple tasks. Therefore, voice-assistant systems may be used, such as that system described in U.S. patent application Ser. No. 12/536,696. Voice-assistant systems provide assistance to a worker, as needed or called upon by the worker.

One such environment that requires greater worker flexibility, and is suitable for voice-assisted work is the work environment in a nursing home or assisted living facility. In such facilities, nurses create care plans for all of the residents or patients, and the care plans define the different tasks to be performed by the workers, such as nurses or certified nursing assistants ("CNAs"), for the residents. In particular, each CNA, for example, has to be aware of and accountable for the tasks in the care plans of the residents that are assigned by the nurses to that CNA. The CNA may control the order in which they choose to address a multitude of tasks and thus take advantage of certain efficiencies in their workflow. The workflow will often depend upon the CNAs environment, their location, the urgency of the task and various other factors, and thus they have great flexibility in performing their work.

As part of the work provided within a medical care facility such as a long-term medical care facility, the various caregivers are often required to capture specific information regarding the care that they provide and to document such care. The information and data that is then captured, pursuant to such a documentation task, provides information for other caregivers and entities to utilize in either follow-up care or further processes, such as billing processes.

One type of documented care that is provided to resident in a long-term care environment involves information about the level of assistance that a resident or patient may need in order to complete a particular life activity. Such activities, including eating, bathing, and toileting, for example, are referred to as Activities of Daily Living (ADL). The information that describes the resident performance and level of assistance that is provided in the ADL is referred to as self-performance and support. Currently, self-performance and support information is captured via extremely inefficient or complicated methods in most of the long-term care industry. For example, such self-performance and support information is often captured via time-consuming, face-to-face interviews with care providers. The care providers are then asked to think back over the past several days or weeks so that they might remember the overall level of assistance that they provided for each resident. As such, the prior art processes produce inaccurate information because of the delay between the time when the care is provided, and the time when the face-to-face interviews with caregivers can take place. The accuracy and completion of the self-performance and support information is critical, because such information is a major factor in determining how a long-term care facility is reimbursed through various programs, such as Medicare and Medicaid programs. Accordingly, it is desirable to obtain accurate and current ADL information for a facility to utilize.

Another drawback associated with existing documentation systems for capturing self-performance and support information is that the various levels for a particular ADL activity are difficult to understand. The different levels have subtle nuances that can easily cause a caregiver to give inaccurate information for a particular activity. In a typical system, there are generally give different self-performance levels or gradations that can indicate the type of self-performance of an activity that a resident might accomplish. Each one of the levels has a set of criteria that determines when it should be used to describe the level of assistance that a caregiver might provide during a particular activity. However, the definition of the levels is difficult to understand. Therefore, the criteria are hard to apply in a consistent manner when such definitions are not well understood. Furthermore, in such a system, there are support levels that go hand-in-hand with the self-performance levels. The support levels may include four or more different designated levels. Furthermore, for each self-performance level, there are, at most, two valid support levels that can be used. As such, the entire concept gets complicated very quickly, and may be difficult to understand by the caregiver, particularly if the caregiver is not constantly doing such documentation.

Furthermore, care providers may have a very low education level, and a very low grade reading level. Often, such care providers are not native English speakers, which present a further hurdle with respect to comprehending all the different self-performance and support level definitions, criteria, and combinations for the purpose of capturing accurate and consistent ADL information for the care that they document.

Accordingly, it is desirable to further assist caregivers in the performance of their daily tasks and also in their generation of the data necessary for proper documentation of the care that is provided. Furthermore, it is desirable to address the drawbacks in the prior art, and to provide the ability to capture current and accurate information associated with activities of daily living (ADL) and the various features of same associated with a resident or patient and a care provider.

SUMMARY OF THE INVENTION

Embodiments of the invention provide for a method and apparatus to properly document ADL information by assisting a care provider in the documentation of self-performance and support information for a person such as a resident or patient. A speech dialog with a care provider is provided using the generation of speech that is played to the care provider and the capture of speech that is spoken by a care provider. The speech dialog provides assistance to the care provider in providing care for a person according to a care plan for the person wherein the care plan includes activities requiring a level of performance by the person. For the activities, speech inquiries are provided to the care provider through the speech dialog. The speech inquiries regard performance of the activity by the person and/or care provider assistance in the performance of the activity by the person. Speech input from the care provider that is responsive to the speech inquiries is captured. From the speech input, a code is determined that indicates the self-performance of the person and support information for a care provider. In that way a care provider is able to accurately document information related to the ADL for a person.

These and other advantages will be apparent in light of the following Figures and detailed description.

BRIEF DESCRIPTION OF THE DRAWINGS

The accompanying drawings, which are incorporated in and constitute a part of this specification, illustrate embodiments of the invention and, together with a general description of the invention given above and the detailed description of the embodiments given below, serve to explain the principles of the invention.

FIGS. 2A-2B is an example of a care plan for a resident that may be generated via a nursing workstation in the voice assistant system of FIG. 1 consistent with the principles of the present invention;

FIG. 3 is a perspective view of one embodiment of a voice assistant of the voice assistant system of FIG. 1 consistent with the principles of the present invention;

Figure 1:
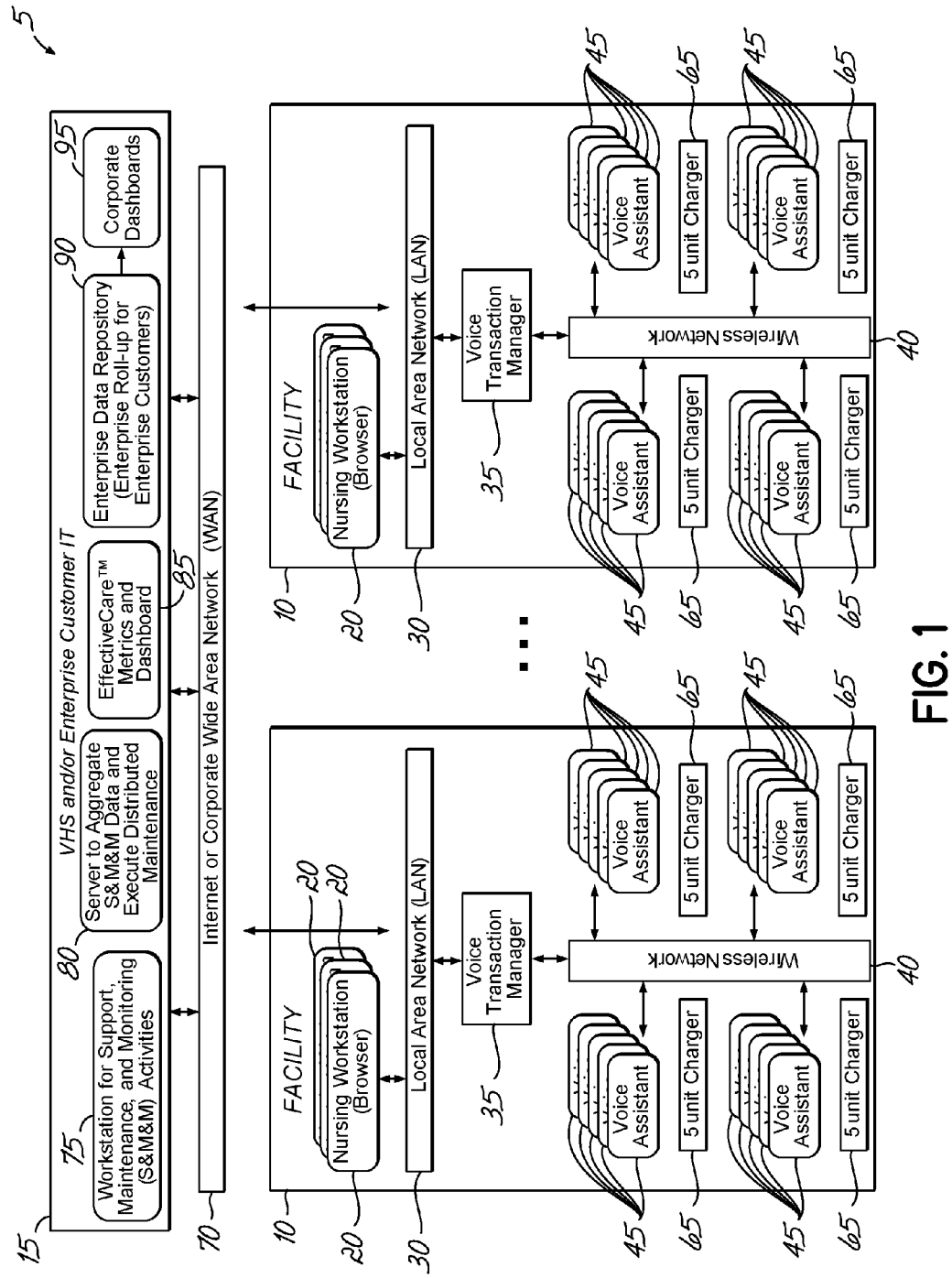
FIG. 1 is a block diagram of a distributed implementation of a voice assistant system consistent with the principles of the present invention.

It should be understood that the appended drawings are not necessarily to scale, presenting a somewhat simplified representation of various features illustrative of the basic principles of embodiments of the invention. The specific design features of embodiments of the invention as disclosed herein, including, for example, specific dimensions, orientations, locations, and shapes of various illustrated components, as well as specific sequences of operations (e.g., including concurrent and/or sequential operations), will be determined in part by the particular intended application and use environment. Certain features of the illustrated embodiments may have been enlarged or distorted relative to others to facilitate visualization and clear understanding.

DETAILED DESCRIPTION

Embodiments of the invention provide a voice assistant system for assisting a user. In some embodiments, the voice assistant assists a CNA or other caregiver or care provider with performing a variety of tasks during the CNA's work shift. It is understood that the voice assistant system may be used in other work environments as well. Consistent with embodiments of the invention, the CNA may engage the inventive voice assistant via a main menu in the form of Situational Awareness Questions, and the CNA may be provided with a speech dialog provides that provides speech inquiries, answers various questions and/or provides other information. As will be readily understood, while a CNA is set forth herein, and discussed as a particular person or care provider to utilize an example of the present invention in a care facility, embodiments of the invention are not limited to a particular user. Alternative users of various embodiments of the invention are anticipated and understood to be beneficiaries of the features disclosed herein. For example, a physician, nurse, and/or other caregiver or care provider in a facility may use various embodiments of the invention.

The CNA may also use various speech commands, and the CNA may be provided with a speech dialog associated to assist the CNA with the execution of a task or used in the performance of an activity involving a person being cared for, such as a resident or patient, for example. Moreover, the voice assistant system may also analyze data received from the CNA and provide a speech dialog at the point of care or the point of execution of an activity that may assist the CNA in the efficiency and accuracy of their work and in documenting their work. Furthermore, the invention provides a care provider with the ability to capture accurate self-performance and support information for the various tasks of activities they perform and document in the course of providing care to a person.

Long-term care facilities and other facilities providing care are able to maximize their potential for reimbursement without having to second-guess or double-check the accuracy of the ADL self-performance and support information captured by the direct caregivers. Also, because of the increased accuracy of the self-performance and support information captured by the direct caregivers, long-term care facilities would have the potential to provide the residents and other persons they care for with better care because an accurate picture of a resident's assistance needs is available.

In one embodiment, the voice assistant system may be and/or may incorporate or include the AccuNurse® software and/or hardware offered by the assignee of this application, Vocollect Healthcare Systems, Inc. ("VHS") of Pittsburgh, Pa. The present invention may be implemented in such a system, and embodiments are described herein for implementing the invention. Additional details of other uses and features of such a system are set forth in the U.S. patent application Ser. No. 12/536,696, which is incorporated herein by reference.

Turning now to the Drawings, wherein like numbers denote like parts throughout the several Figures, FIG. 1 is a diagrammatic illustration of a voice assistant system 5 that may be in the form of a distributed computing system, with computing activities associated with at least one onsite nursing home or assisted living facility as at 10. The nurses, CNAs, care providers, and residents, patients, or other persons of a facility are typically physically located at the facility 10, while centralized support and management capabilities for the voice assistant system 5 may be provided by an offsite VHS department and/or by an onsite enterprise customer IT department 15.

As illustrated, the voice assistant system 5 may include more than one facility 10, and each facility 10 may be subdivided into a plurality of units. All of the units may be referred to as a site, but will generally be referred to as the facility 10 for simplicity, unless otherwise stated. Also for simplicity, the discussion will primarily focus on a single facility 10 and its respective nursing workstation 20, voice assistants 45, and chargers 65 (discussed further hereinbelow), even though a plurality of these items are illustrated in FIG. 1. Those of ordinary skill in the art will appreciate, however, that embodiments of the invention may apply equally to the other facilities (including other nursing workstations, other voice assistants, and other chargers) in the voice assistant system 5. Furthermore, the discussion of embodiments of the invention will be from the perspective of a single CNA utilizing the voice assistant 45 for simplicity, but those of ordinary skill in the art will appreciate that each CNA and/or each nurse may have a voice assistant 45.

Turning to the facility 10, at least one care plan is generated by a nurse or other qualified personnel for each resident at the facility 10. In one feature of the present invention, interactive care plans are created and maintained for interacting with the voice assistant 45. As such, the care plans may be accessible through the nursing work station 20. The information of the care plans may be accessed by the voice assistants 45 to assist the CNAs, by voice, in the various tasks associated with the care plans. Advantageously, it is believed that this is a significant improvement over the use of written care plans that are typically located in various binders at a nursing station. It is worth noting that the CNAs may not be authorized to generate and/or change care plans, but the CNAs can view and perform the tasks in the care plans. To generate and/or revise care plans, the facility 10 may include at least one nursing workstation 20, and a nurse or other qualified personnel associated therewith may generate and/or revise a care plan as needed via a graphical user interface, such as an application displayed via a web browser, associated with the nursing workstation 20. Specifically, the application displayed may display a variety of information for the nurse to select, including pull-down menus, boxes, etc. Using the pull-down menus, boxes, etc., the nurse may generate and/or revise a care plan as needed. FIGS. 2A and 2B illustrate an exemplary care plan 25 for the activity of toileting for a resident named Jane Doe as displayed in the application. Specifically, FIGS. 2A and 2B illustrate an exemplary care plan 25 prior to a nurse saving the changes to the toileting care plan. Various other care plans will exist as well associated with other activities and activities of daily living (ADL). For example, the care plans might be directed to Ambulation of the Resident, Background Information, Bathing, Dressing, Personal Hygiene, Meals, Medical Precautions, Mood/Behavior, Positioning, Transfers, and Vitals and Weight, for example. However, one of ordinary skill in the art will appreciate that there may be additional care plans for other activities, tasks and/or information. Each care plan may have various menus, boxes, and other selectable fields for entering or selecting information and parameters for the care plan. The care plans may be displayed via the application in the web browser, and the care plans may direct the workflow of the CNA via the voice assistant 45 (discussed further hereinbelow). The care plans for a particular resident may determine what tasks the CNA must perform for that resident during the shift. The care plans also are part of the overall system for documenting information associated with an ADL activity.

Furthermore, the nursing workstation 20 may also be utilized to generate and/or update work assignments for the CNAs. For example, before the start of the shift of a particular CNA, the nurse or other qualified personnel in the facility 10 (or unit thereof) may set up and/or update the work assignment for the CNA via the nursing workstation 20. As such, the nurse or qualified personnel may set up and/or update a work assignment for the CNA to include an assignment of specific persons or residents to that CNA for a shift or appointments associated with the CNA (including an appointment with a resident), as well as make changes to a care plan for a resident. The nurse or other qualified personnel may also print out an exception report from the nursing workstation 20 that indicates the tasks that still need to be performed by a CNA.

The nursing workstation 20 may represent practically any type of computer, computer system, appliance, or other programmable electronic device. The nursing workstation 20 may also be capable of functioning as a client and/or server or may be implemented using one or more networked computers, e.g., in a cluster or other distributed computing system. In some embodiments, the nursing workstation 20 may be similar to a client computer.

Figure 1A:
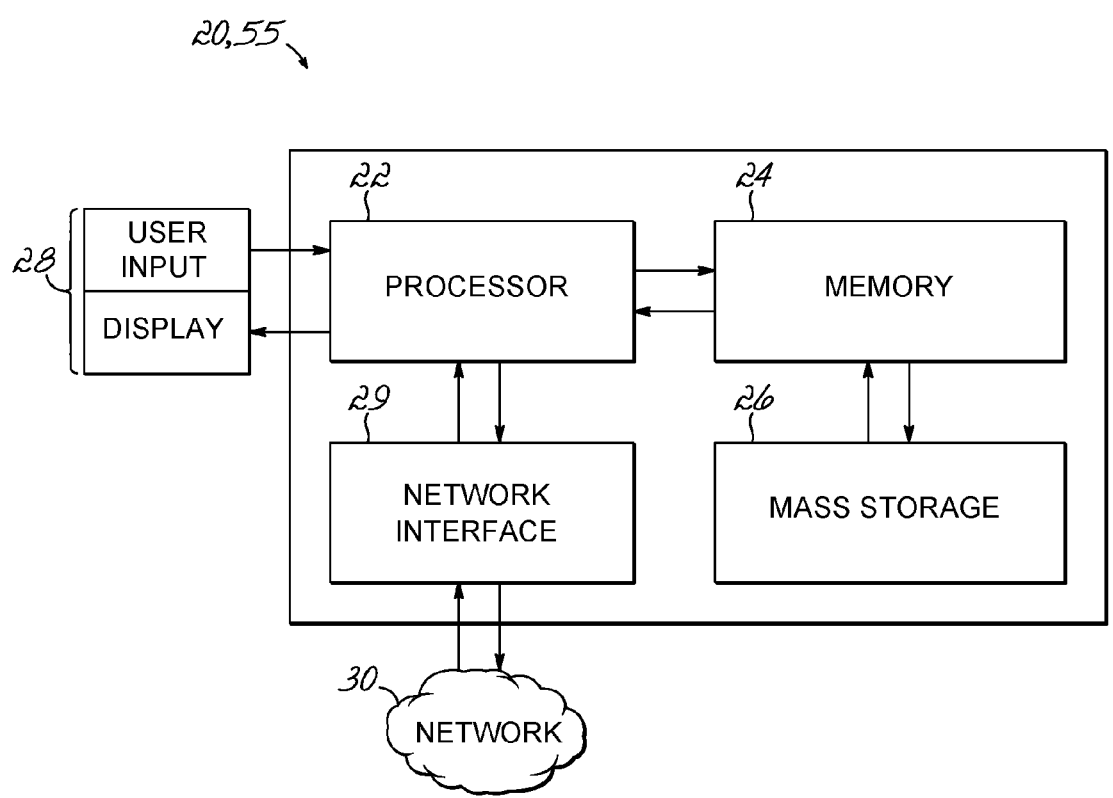
FIG. 1A is a block diagram of a basic computer that might be implemented in the system of FIG. 1 consistent with the principles of the present invention.

Along with the web browser, the nursing workstation 20 computer, as shown in FIG. 1A, may also include an operating system, at least one processor 22, such as a central processing unit (CPU), a memory 24, mass storage 26, a user interface 28, with appropriate user inputs and displays, a network interface 29, and/or routines that are configured to be executed to implement the embodiments of the invention, whether implemented as part of an operating system or a specific application, component, program, object, module or sequence of instructions, or even a subset thereof, which will be referred to herein as "computer program code", or simply "program code." Program code typically comprises one or more instructions that are resident at various times in various memory and storage devices in a computer, and that, when read and executed by one or more processors in a computer, cause that computer to perform the steps necessary to execute steps or elements embodying the various aspects of the invention.

The information associated with at least one care plan may be transmitted (e.g., in digital form) from the nursing workstation 20 (e.g., using the network interface) via a local area network (LAN) 30 to a voice transaction manager 35. Each facility 10 may have at least one voice transaction manager 35 to store the care plans and facility configuration information. Specifically, the voice transaction manager 35 may represent and/or include practically any networked appliance, device, or computer as described hereinabove in connection with the nursing workstation 25. As such, and in some embodiments, the voice transaction manager 35 may include a web server and/or a database server as is known to a person of ordinary skill in the art. Thus, the voice transaction manager 35 may include at least one database for storing the data, which may in turn be transmitted from the voice transaction manager 35 to the nursing workstation 20.

Furthermore, in one embodiment of the invention, Solaris may be utilized as the native operating system in the voice transaction manager 35, but no explicit operating system dependencies may be required for the web server and/or the database server. Java may be utilized as the native programming language of the voice transaction manager 35, and the voice transaction manager 35 may be implemented and managed using conventional Internet technologies. The voice transaction manager 35 may also function as backup in case of data loss. From the perspective of the care providers, like nurses and CNAs, the voice transaction manager 35 may not require onsite IT maintenance beyond turning the power on and off. Furthermore, a type of network other than the LAN 30 may alternatively be utilized to transmit data from the nursing workstation 20 to the voice transaction manager 35.

Referring back to FIG. 1, the facility 10 may also include at least one charger 65 to charge the voice assistant 45. As illustrated in FIG. 1A, each charger 65 may charge up to five voice assistants 45. Furthermore, a least one item in the facility 10 may transmit and/or receive data via the Internet or a corporate wide area network (WAN) 70 to the offsite Vocollect Healthcare Systems, Inc. (VHS) department and/or the onsite enterprise customer IT department 15.

The offsite VHS department and/or the onsite enterprise customer IT department 15 may include a workstation for support, maintenance and monitoring (S&M&M) activities 75 as well as a server to aggregate S&M&M data and execute distributed maintenance 80. The offsite VHS department and/or the onsite enterprise customer IT department 15 may further include metrics and at least one dashboard 85 such as EffectiveCare™ offered by VHS, an enterprise data repository that may be utilized for enterprise roll-up for enterprise customers 90 and/or at least one corporate dashboard 95. For example, the offsite VHS department may be able to remotely maintain the voice transaction manger 35, provide other remote support, and/or monitor performance of the voice assistant system 5.

In short, the voice assistant system 5 may emphasize distributed execution, but centralized platform management and data roll-up, as discussed hereinabove. Moreover, those of ordinary skill in the art will readily appreciate that other functionality may be possible as well. Those skilled in the art will recognize that the exemplary environments illustrated in FIGS. 1-1A, 2A-2B and 3 are not intended to limit the present invention. Indeed, those skilled in the art will recognize that other alternative hardware and/or software environments may be used without departing from the scope of the present disclosure.

Next, the information and data associated with at least one of the care plans in the voice transaction manager 35 may be transmitted (e.g., in digital form) from the voice transaction manager 35 (e.g., using the network interface) via wireless network 40 (e.g., a wireless local area network, or "WLAN") to at least one voice assistant 45. Data may also be transmitted from the voice assistant 45 to the voice transaction manager 35, for example, for storage and/or processing at the voice transaction manager 35.

The voice assistant 45 of one embodiment may include three separate portions, including a headset portion (e.g., including a microphone, one or more earpieces, and one or more speakers), a device portion and a connecting portion. In some embodiments, the connecting portion may be a cable or a wireless link. Although the voice assistant 45 shown in the Figures has multiple different portions, the voice assistant 45 may represent and/or include practically any networked appliance, device, or computer as described hereinabove. An exemplary voice assistant 45 with a headset portion (or "headset") 50, a device portion (or "portable computer portion") 55, and a connecting portion such as a cable 60 that couples the headset portion 50 to the device portion 55 is illustrated in FIG. 3. In alternative embodiments, the headset 50 is coupled to the device portion 55 through a wireless link, which may also be referred to as a "connecting portion." In a further alternative embodiment, the functionality of the device portion 55 may be incorporated into the headset 50 such that voice assistant 45 is one self-contained piece of equipment. As will be understood by a person of ordinary skill in the art, the headset incorporates an appropriate speaker 52 to play speech to the care provider or other user and a microphone 54 to capture speech spoken by the user. The played and captured speech is part of an ongoing speech dialog to implement the invention and to implement the various care plans for various persons/residents in a facility.

The voice assistant 45 may also include at least one database 26 to store data received from the voice transaction manager 35. A speech dialog is implemented utilizing the data in the database, and the data in the database may be utilized to generate a speech dialog wherein speech is generated and played to the care provider and speech that is spoken for certain commands (e.g., a "Review" command) and to store data from the user with respect to other commands (e.g., a "Document" command). The speech dialog may include at least one statement generated by the voice assistant 45.

In some embodiments, the voice assistant 45 is a wearable computer and/or a personal digital assistant (PDA) that includes WLAN capabilities or other network capabilities. As would be understood by a person of ordinary skill in the art, such a computer would include at least one processor, such as a central processor unit, a memory, one or more user interfaces for input/output functionalities, and/or routines or other software that is configured to be executed to implement the embodiments of the invention, whether implemented as part of an operating system or a specific application. As noted above, such software is referred to as computer program code, or simply program code, and then a computer will generally comprise one or more instructions that are resident to various times and various memory and storage devices in a computer, and that, when read and executed by one or more processors in the computer, cause that computer to perform the steps necessary to execute the steps or elements that embody the various aspects of the invention. Again, FIG. 1A illustrates basic components of a typical computer suitable for the device portion 55 of voice assistant 45.

Alternatively, the voice assistant 45 may be a voice appliance that is deployed to perform specific functions for the CNA via a main menu associated with the voice assistant 45, instead of being deployed for a general purpose. In particular, the voice assistant 45 may be a client, and more specifically a "thick client" that is configured to perform speech recognition and speech synthesis. As such, and in some embodiments, the voice assistant 45 may be similar to a client computer.

Figure 4:
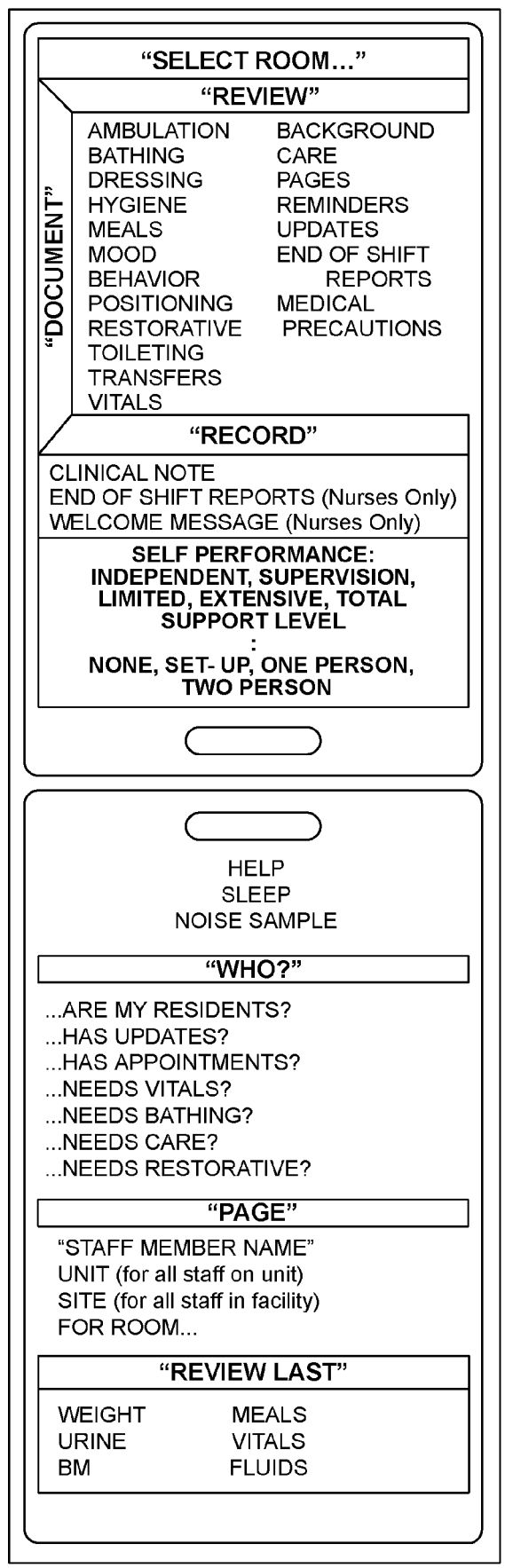
FIG. 4 is one example of a document with information regarding interacting with the voice assistant system of FIG. 1 consistent with the principles of the invention.

In accordance with the principles of embodiments of the invention, each CNA at the facility 10 may have their own voice assistant 45 that they wear or carry. When a CNA connects the headset portion 50 to the device portion 55 via the connecting portion 60, or when a CNA turns the voice assistant 45 on, this may activate the voice assistant 45 and "log" the CNA on to the voice assistant system 5 (e.g., establish a connection between the voice assistant 45 and the nursing workstation 20 and/or voice transaction manager 35, as well as determine which particular CNA is logging onto the voice assistant system 5 based on an identification associated with the CNA and/or the voice assistant 45, and retrieve data associated with that particular CNA and/or voice assistant 45). In response to logging the CNA on to the voice assistant system 5, one or more items may be transferred from the voice transaction manager 35 to the voice assistant 45. These items may include the list of residents assigned to the CNA for the shift, the care plan data for all of the residents assigned to the CNA, the appropriate voice templates and/or the facility configuration information, such as, but not limited to, the list of CNAs generally assigned or logged into the current shift. Moreover, the CNA may physically carry a document (e.g., document 62 illustrated in FIG. 4) that sets forth the speech vocabulary to interact with the voice assistant 45 (e.g., including the main menu 63 illustrated in FIG. 5). In particular, the CNA may use the voice assistant 45 to interact with the main menu by selecting from the predefined parameters in the form of speech input (e.g., including Situational Awareness Questions, commands and/or other vocabulary, at least a portion of which is illustrated on the document 62). The speech recognition capabilities of the voice assistant 45 receives the speech input and utilizes the speech recognition capabilities to convert the speech input into machine readable input (e.g., data that can be processed by the voice assistant 45 or another portion of the voice assistant system 5, including the nursing workstation 20 and/or voice transaction manager 35, for example). The speech synthesis capabilities of the voice assistant 45 may then provide speech dialog in response to the speech input (e.g., answers to a Situational Awareness Question and/or speech dialog in response to a command and/or other vocabulary, for example). Furthermore, the voice assistant 45 may also be utilized to provide the CNA with audible tones and/or speech dialog in response to various statuses, as discussed further in U.S. patent application Ser. No. 12/536, 696.

It is worth noting that the care plans for the residents and various of the ADL activities typically remain stable from day to day and from shift to shift. For example, a resident needs to eat meals every day, go to the bathroom (toileting) every day, etc. A care plan may change if the nurse makes the change at the nursing workstation 20, as the CNA cannot generally change the care plans on his or her voice assistant 45, as discussed above. As such, care plans may be received by the voice assistant 45 at the start of every shift and/or upon activation to reflect any changes to the care plans that occurred prior to the start of the shift and/or activation, and the care plans may be dynamically maintained throughout the shift and/or activation to include any changes.

As the CNA completes the different tasks associated with the items in the care plans, a data set reflective of the work completed by the CNA may be generated at the voice assistant 45. The data set may be utilized for various purposes. For example, the data set may be utilized to answer the questions of the CNA (e.g., the answer may be based on the data set alone or the answer may be based on the data set and the care plans), to generate a historical report, to generate an MDS, and/or to generate an exception report (e.g., at the nursing workstation), and to generate necessary reports for reimbursement, among other purposes. Thus, the care plans on the voice assistant 45 are not configured to track the completed tasks or changes in response to the completion of work by the CNA. Rather, it is the generated data set that tracks completed work. Indeed, a new data set may be generated during each shift.

Accordingly, data is captured pursuant to the ongoing speech dialog in the voice assistant system, as implemented in utilizing the voice assistants 45 carried, worn, or otherwise implemented by a care provider. Utilizing the data that is captured through the voice assistant system 5, various reports, such as MDS reports, Exception Reports, Historical Reports, and other documentation may be generated. Such reports and documentation will include information and data that is necessary to determine how much money a facility will receive in the form of reimbursement from program such as Medicare and Medicaid. In accordance with one aspect of the invention, one set of information captured by the invention is self-performance and support information regarding ADL activities performed by a person or patient. For example, a care plan may include one or more activities that require a level of performance by the person or patient to whom the care is being provided. As the care is provided and the activity is completed, a care provider will provide input data and information, through the speech dialog, regarding the particular activity. For example, one command that might be implemented through the speech dialog in the voice assistant system 5 of the invention is the "Document" command.

Figure 5:
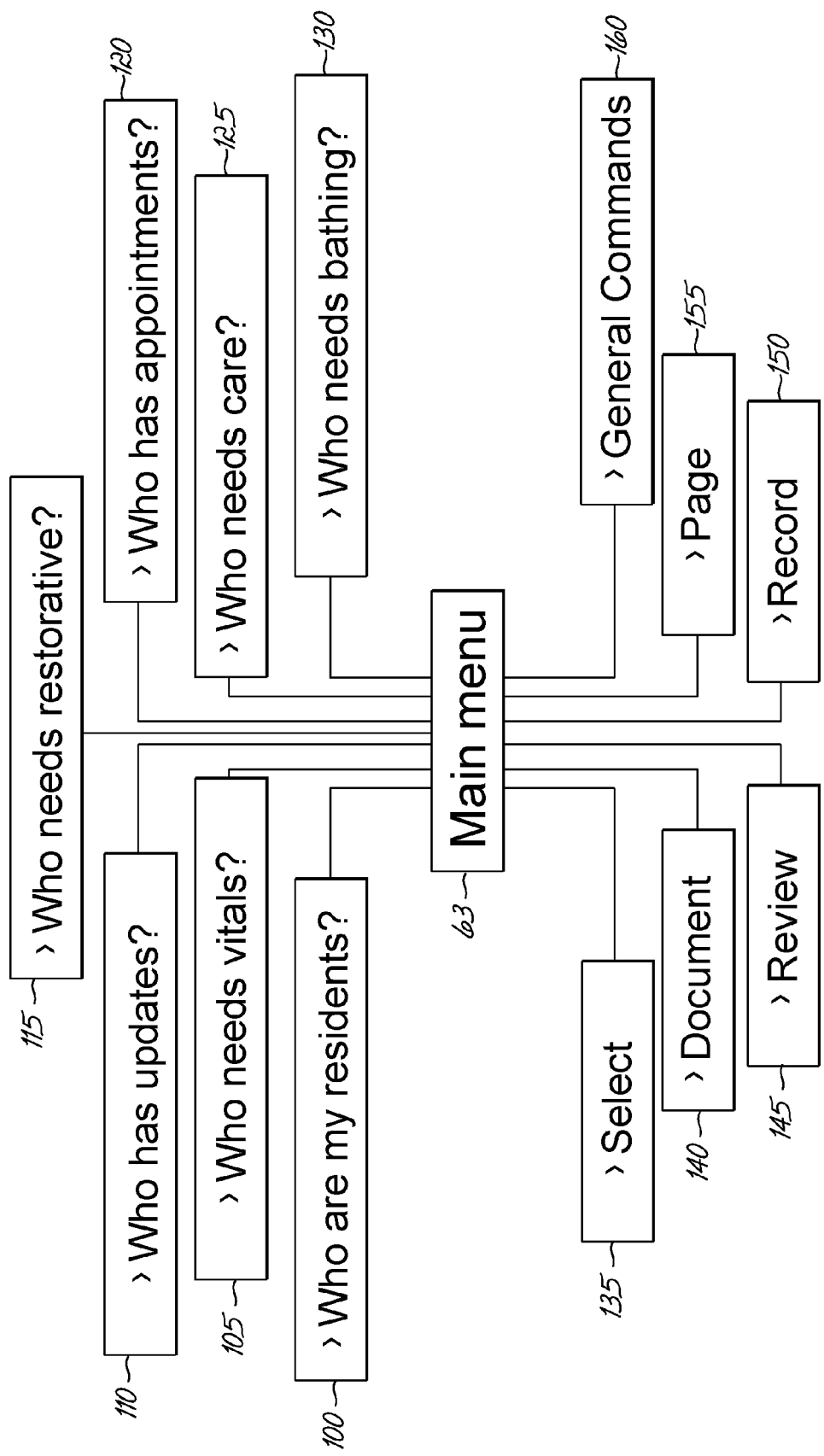
FIG. 5 is one embodiment of a main menu that a user may interact with, consistent with the principles of the present invention.

Turning now to FIG. 5, via the main menu 63, the CNA may select at least one parameter through speech input that corresponds to a command. The speech recognition capabilities of the voice assistant 45 are utilized to receive the speech input of the user and determine the parameter or command selected by the CNA. In general, the commands may be associated with various tasks and invoked by the CNAs for assistance with, and for execution of, pending tasks or activities of the person to whom care is provided, such as ADL activities. Various exemplary commands are illustrated as commands 135-160 in FIG. 5. Respectively, in on embodiment, these are "Select" (block 135), "Document" (block 140), "Review" (block 145), "Sleep" (block 147) "Record" (block 150), "Page" (block 155) and General Commands (block 160). Furthermore, each of these commands may have additional sub-commands and/or sub-categories associated with them.

For example, the "Review" command may have a sub-category for "toileting" to review the toileting of a resident. Similarly, the "Document" command may have a sub-command for "meals," the "Page" command may have a sub-command for "unit," etc. However, those of ordinary skill in the art will appreciate that additional commands other than those listed may also be supported.

For at least some commands, such as the "Document" command, speech dialog is provided that corresponds to that command. For example, the speech dialog for the "Document" command will enable the care provider to capture information. The speech dialog may include asking the user to speak at least one input, repeating the CNAs input, etc. The speech dialog may be based upon the data stored in the voice assistant 45, including the care plans and/or voice templates. Such dialogs may be generated by the voice transaction manager 35 and/or the voice assistant 45 using speech synthesis, or text-to-speech (TTS), as is known to a person of ordinary skill in the art. The text of the speech dialog may depend on the specific command and the data requested by the voice assistant 45, or the information to be provided by the voice assistant 45. As may be appreciated, the speech dialog takes various different forms to provide information about a resident or a care plan to a CNA, or to obtain information and data about a resident pursuant to their care plan.

Figure 6:
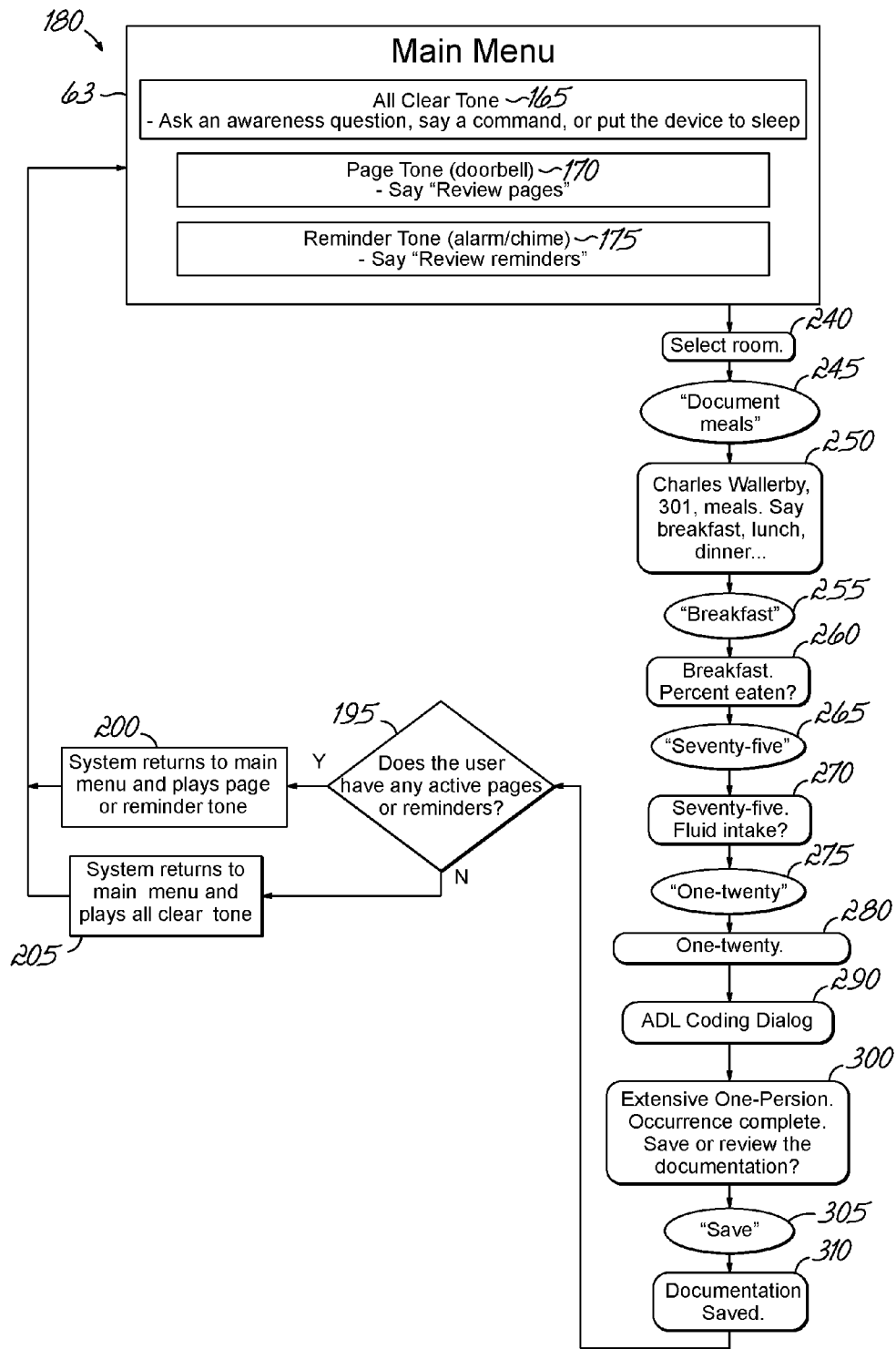
FIG. 6 is an exemplary main menu routine executed by the voice assistant system of FIG. 1 for documenting an activity consistent with the principles of the present invention.

Turning now to FIG. 6, that Figure illustrates an exemplary voice dialog and workflow routine 180 executed by the voice assistant system 5 depicting interaction between the CNA and the main menu 63. First, the CNA logs on and the care plans of the assigned residents and the facility configuration data, as well as any other pertinent data, may be sent to the voice assistant of the CNA. After logging on, the CNA may hear the all clear earcon indicating that there are no active pages or reminders, and the CNA may "sit" in the main menu 63 of the voice dialog until the CNA desires to ask a Situational Awareness Question, say a command, or put the voice assistant 45 to sleep. While the CNA sits in the main menu 63, the voice assistant 45 may be awake and using its speech recognition capabilities to actively listen for speech input, interpret the speech input and/or determine if the CNA has spoken a valid parameter that is used in the voice dialog of the invention. The CNA may put the voice assistant 45 to sleep when the CNA wants to speak (e.g., to a resident) but does not want the voice assistant 45 to use its speech recognition capabilities and other functionalities. In some embodiments, the voice assistant 45 enters a sleep mode after a predetermined time during which it is idle (e.g., including at the main menu 63), such as, for example, about 20 seconds.

As discussed in U.S. patent application Ser. No. 12/536, 696, entitled "VOICE ASSISTANT SYSTEM", the care provider may maintain the speech dialog with the voice assistant 45 or other device to perform a variety of different tasks, obtain information, and otherwise manage their workload with respect to providing care to one or more persons within a facility. As noted above, proper documentation of the care that is provided is necessary not only for keeping accurate records, but also for insuring that a facility is suitably reimbursed through various reimbursement programs. To that end, the present invention is directed to improving documentation, and particularly to accurately capturing documentation related to the self-performance and support information for a person who may be performing a particular ADL activity associated with their daily living regimen, and with which a care provider is engaged.

Figure 7:
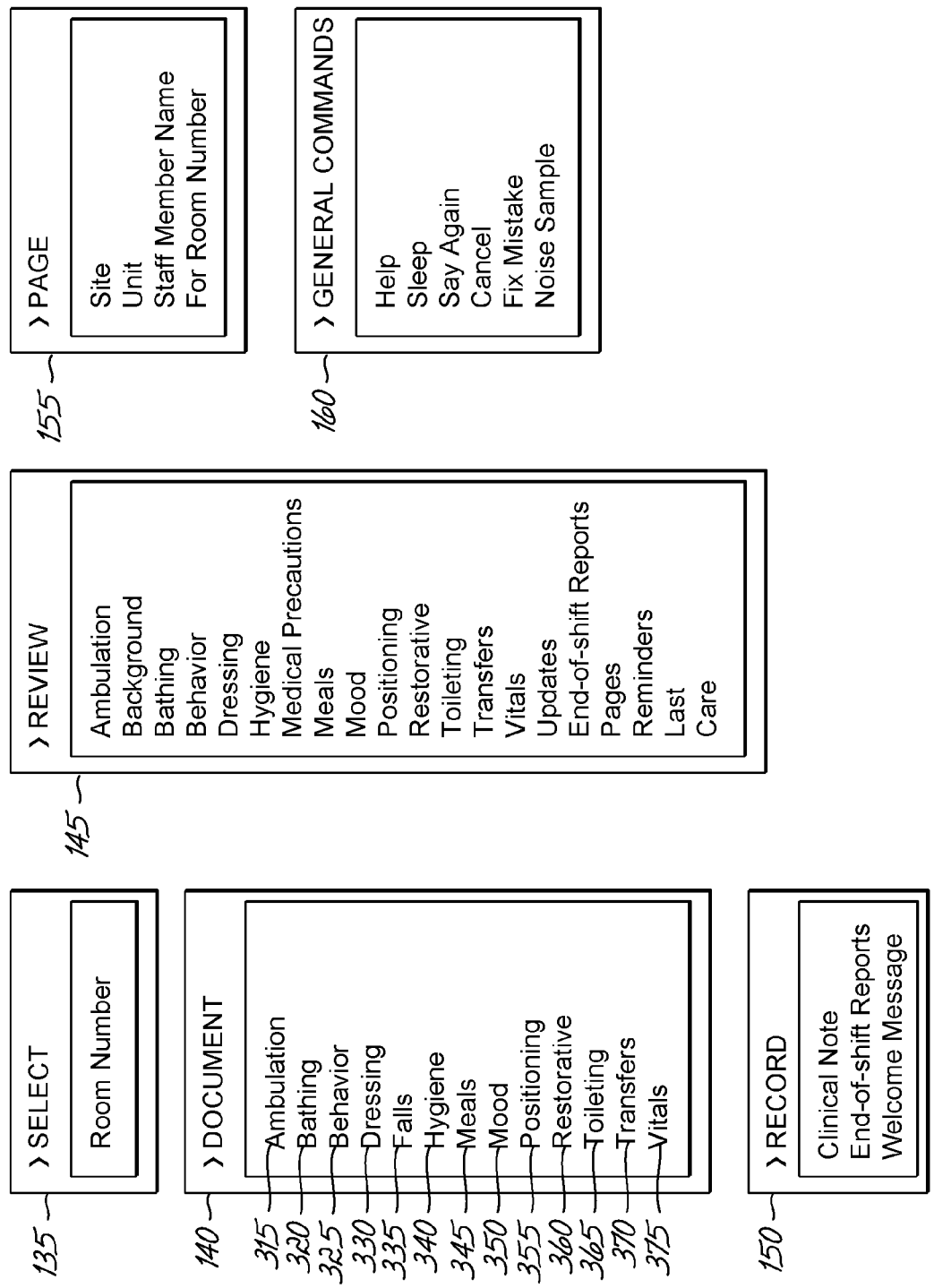
FIG. 7 is a detailed view of the parameters in the form of commands from the main menu of FIG. 5 consistent with the principles of the present invention.

For the daily living regimen of a person or resident within a care facility, various ADL activities are performed by the person with or without assistance of a care provider. It is those particular activities that provide part of the care plan for a resident, and which would be reviewed and documented by a care provider. Referring to FIG. 7, the command to "Document" an activity within the speech dialog will generally be associated with a particular sub-command within the overall "Document" command. In that way, documentation may be captured, using the speech dialog, for a variety of different activities and tasks that are performed by the resident.

Figure 8:
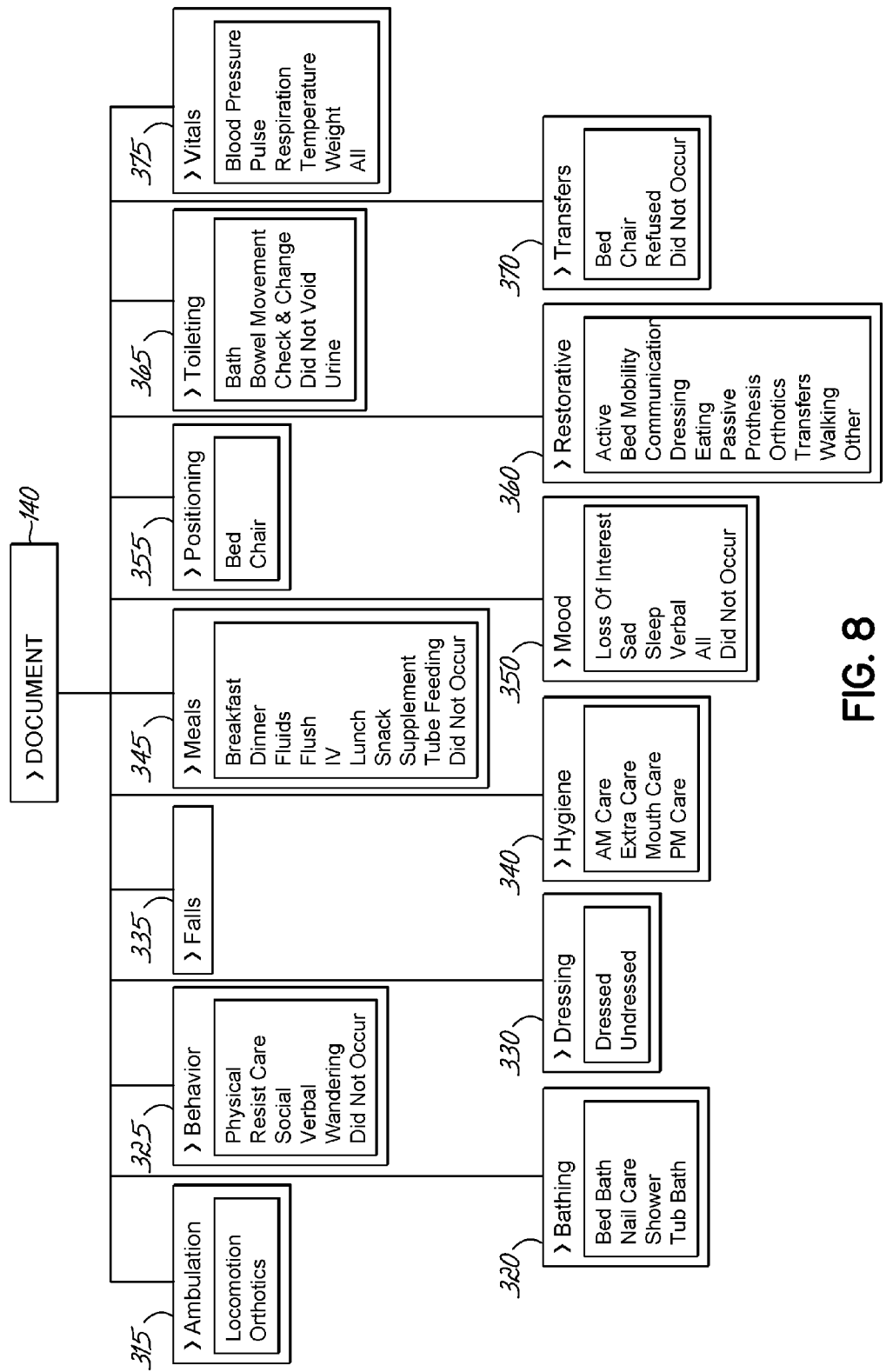
FIG. 8 is a detailed view of the Document command from FIG. 8 consistent with the principles of the present invention.

While the example in FIG. 6 addresses documenting a meal task or activity, other activities may be documented as well. FIGS. 7-8 illustrate in more detail some of the commands, sub-commands, and information that the CNA may choose via the main menu 63 and particular sub-commands for the "Document" command. One of ordinary skill in the art will appreciate that the commands and sub-commands are utilized to facilitate discussion related to the embodiments of the invention consistent with the principles of the present disclosure, but not otherwise intended to be limiting. Similarly, one having ordinary skill in the art will appreciate that the information that may be chosen by the CNA in response to the speech dialog provided is also not intended to be limiting. FIGS. 7-8 are merely illustrative of details of various items, with the hierarchy from broadest to narrow being command, sub-command, and information. Furthermore, those of ordinary skill in the art will appreciate that each command and sub-command combination may be associated with a separate executable routine and may provide different speech dialog as necessary to facilitate the task.

Referring to FIG. 7, the "Select" command 135 may be utilized to select a room number, and then the "Document" command 140 or the "Review" command 145 may be chosen by the CNA. With the "Document" command 140, a variety of tasks indicated by the various resident care plans may include ADL activities to be performed by a resident and assisted or performed by the CNA and documented via the "Document" command 140 and the sub-commands that correspond with that task. Some of the sub-commands are illustrated under the "Document" command 140 in FIG. 8. The sub-commands may be, but are not limited to, "ambulation" 315, "bathing" 320, "behavior" 325, "dressing" 330, "falls" 335, "hygiene" 340, "meals" 345, "mood" 350, "positioning" 355, "restorative" 360, "toileting" 365, "transfers" 370, and/or "vitals" 375. Various of the sub-commands correspond to the care plans and ADL activities. And each one of these sub-commands may have information for the CNA to choose, as illustrated in FIG. 8. For example, the CNA may choose the "Document" command 140 and the "ambulation" sub-command such that the CNA is then engaged and prompted by the speech dialog associated with the combined "Document ambulation" commands. Part of that dialog may be to further select sub-commands or activities, such as to choose between locomotion or orthotics for documentation purposes (FIG. 8). Next, the CNA may be provided with the appropriate speech dialog based upon whether locomotion or orthotics was chosen. Such a speech dialog may, for example, consist of a series of questions for the CNA to answer as set forth in the example of FIG. 6.

In another example, the CNA may choose the "all" term as illustrated in FIG. 8 to document all of the information for a certain sub-command, like "vitals" 375 or "mood" 250. Also, in some instances, the CNA may have to choose the "did not occur" terminology to affirmatively document that a task did not occur (e.g., "meals" 345 or "transfers" 270), or the "did not void" terminology for "toileting" 365 to indicate that the resident did not have to go to the bathroom (see FIG. 8). In this way, various different activities, including ADL activities, may be documented, such as for reimbursement purposes.

Figure 9:
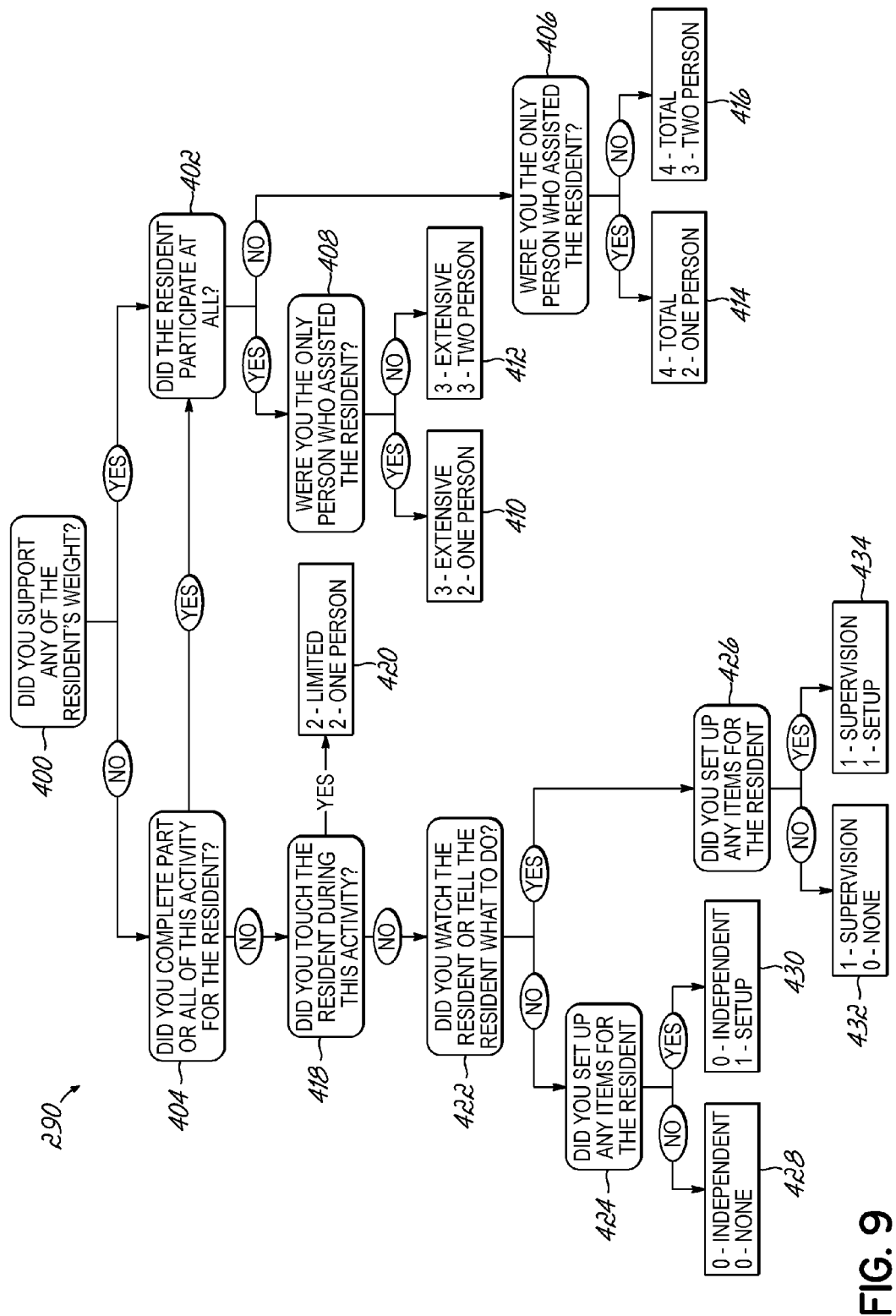
FIG. 9 is an exemplary illustration of and ADL coding dialog executed by the voice assistant system of FIG. 1 consistent with the principles of the present invention.

Referring to FIG. 6, a "Document" command example is illustrated. To complete tasks for a resident and document those tasks, the CNA may say "Select Room 301" (block 240), which is Charles Wallerby's room number, and then state "Document meals" (block 245). As such, the CNA may be provided with a speech dialog that corresponds to the "Document meals" command/sub-command, such as that illustrated in blocks 250, 260, 270, 280, 290, 300, and 310. In accordance with one embodiment of the invention, at block 290, the speech dialog may implement an ADL coding dialog or sub-dialog routine as part of the overall dialog. Referring to FIG. 9, the flow of the ADL coding speech dialog is shown for assisting a care provider in the documentation of self-performance and support information for a resident or other person. In the past, the speech dialog may simply have asked the care provider to speak or give both the self-performance level, as well as the support information, so that it may be captured and documented. However, such a system was subject to the lack of knowledge of the care provider, and mistakes and errors associated with assessing the proper self-performance information and categories and the proper support information would occur. Accordingly, the present invention guides the care provider to a more accurate self-performance and support assessment so that the proper code indicating the self-performance and support information can be captured for ADL activities. Although FIGS. 6 and 9 indicate the ADL coding dialog as a separate dialog or sub-dialog, it will be understood that it can be part of the overall "Document" dialog rather than a sub-dialog.

In FIG. 6, block 250 acknowledges the intentions of the CNA to "Document meals" and indicates the predetermined vocabulary that the CNA may say when documenting a meal by stating "Charles Wallerby, 301, meals. Say breakfast, lunch, dinner . . . " After the CNA says "breakfast" (block 255), block 260 acknowledges the documentation of the breakfast meal and requests the CNA to indicate the percentage eaten by Charles Wallerby by stating "Breakfast. Percent eaten?" The CNA may respond with "Seventy-five" (block 265) to indicate 75%, and may then hear "Seventy-five. Fluid intake?" (block 270). The CNA may respond to this request with "One-twenty" (block 275) and may then hear "One-twenty". The speech dialog then progresses to determine ADL information. In the illustrated example, the dialog progresses to the ADL coding routine of FIG. 9. As may be appreciated, the ADL coding dialog is additional speech dialog that is implemented to assist and guide the care provider. It will usually be implemented in a seamless fashion in the "Document" command speech dialog, but is illustrated as a separate routine/dialog in FIGS. 6 and 9 for purposes of discussing the inventions features. After the ADL coding dialog and the determination of the appropriate codes, the dialog may state the determined code or its meaning, such as "Extensive. One Person." Occurrence complete. Save or review the documentation?" (Block 300). In that way, various data associated with a particular task is handled and documented by the voice assistant. It will be appreciated that alternative values other than those illustrated and described herein may be documented without departing from the scope of embodiments of the invention.

As may be appreciated, other data associated with other care plan segments may be captured in similar fashion with other appropriate voice dialogs that are reflective of the particular care plan and the fields therein. For example, "Document hygiene" may have a voice dialog associated with that portion of the care plan.

As noted, the self-performance and the support levels generally refer to the amount of assistance that the resident needed, and may vary based upon the activity. The different self-performance levels may be illustrated in document 62 in FIG. 4 to assist a care provider, along with the Situational Awareness Questions and commands that the CNA may say. However, with the invention, even such notes regarding self-performance and support may be less necessary. Next, the CNA may say "Save" (block 305) and may then hear "Documentation saved." (block 310). Control may then pass to the blocks 195, 200 or 205 as appropriate, and then to the main menu 63 as described hereinabove.

Referring to FIG. 9, a flow from one example of the ADL coding speech dialog or sub-dialog 290 is illustrated. As noted with respect to FIG. 6, the speech dialog is provided by using generation of speech to play to and be heard by the care provider and the capture of speech spoken by the care provider. The speech dialog provides assistance to the care provider when they are providing care for a person according to a care plan for that person. Generally, the care plan will include one or more activities, such as ADL activities that require a level of performance by the person or resident being care for. As the activity is being completed and the care provider is assisting (or not assisting) the person or resident in the completion of the activity or tasks, the care provider is able to document the self-performance characteristics or levels associated with the performance of the person, and is also able to document the support characteristics or levels of the support that the care provider provides to the person/resident in completion of the activity or task. To that end, speech inquiries are provided or made to the care provider, through the speech dialog. Those speech inquiries regard the performance of the activity by the person or resident. Also, speech inquiries are provided to the care provider, through the speech dialog, regarding care provider assistance that is offered to the person in the performance of the activity by that person. The care provider speaks and answers the inquiries, and thus, providers speech input that is responsive to the speech inquiries. As a result of the inquiries, speech input from the care provider is captured. The speech input is generally responsive to the speech inquiries, such as to answer specific inquiries. In accordance with one aspect of the invention, a code is determined from the speech input that indicates the self-performance of the person, and the support information for a care provider. The code will generally be reflective of the information gathered with respect to the self-performance and support information associated with the activity. With respect to generated ADL codes, as provided by one embodiment of the invention, they are reflective of the ability of a resident to perform the activity on their own and a level of support that the care provider must give to the person in the completion of their activity. As is illustrated in FIG. 9, those codes may be reflected numerically or grammatically with respect to the various levels of self-performance and support.

In the embodiment of the ADL coding dialog 290 illustrated in FIG. 9, an inquiry is made in block 400 to the care provider regarding whether they supported any of the resident's weight. An answer is provided by the care provider as speech input. If they did, as illustrated by block 402, a further inquiry is made as to whether the resident participated at all in the activity. If the resident's weight was not supported, an inquiry is made regarding whether the care provider completed part or all of the particular activity for the resident, as illustrated in block 404. As part of the exemplary illustrated speech dialog, the present invention provides a straightforward YES/NO dialog aspect so that a care provider can be simply and directly brought to the proper ADL coding and documenting regardless of the care provider's understanding of particular levels of self-performance and support. Other embodiments of the invention might use or allow other speech inputs, and the invention is not limited to the illustrated dialog. If the resident did not participate at all or actually did participate, an inquiry is made, as illustrated in blocks 406 and 408, as to whether the current care provider is the only person who assisted the resident. Depending upon the answer or speech input for such an inquiry, the support information will indicate whether one person or two persons provided support. Also, since the path reflected in block 402 is taken if the resident's weight has to be supported, depending on the path to blocks 406 or 408, the self-performance will be indicated as low, with either extensive assistance by a care provider or total assistance. As indicated by blocks 410, 412, 414, and 416, the particular ADL code will be generated as illustrated with certain numerical designations for the self-performance and support information. For example, the designation of extensive assistance for self-performance is set forth with numeral 3, whereas the designation of total assistance is designated with the numeral 4. Similarly, one-person assistance is designated with numeral 2, and two-person assistance is designated with numeral 3. As illustrated in block 414, for example, an ADL code of 4, 2 would indicated that the assistance to the resident was total (i.e., low self-performance), and only one care provider was necessary for such assistance.

Referring to block 404, if the resident's weight was not supported, and the care provider did complete part or all of the activity for the resident, the dialog flow may return to block 402 as the self-performance of the resident or person would be in a lower-coded category. However, if the care provider did not have to complete part or all of the activity, the self-performance would be in a higher-coded category, as indicated by the further dialog flow. For example, in block 418, an inquiry is made regarding the care provider assistance in the performance of the activity by the resident. Specifically, an inquiry is made regarding whether the care provider touched the resident during the activity, which would indicate some assistance. If the answer to that inquiry is "YES", the ADL code would indicate that the self-performance was limited, and the support was only one person, as indicated by block 420. Generally, each of the dialog blocks will provide a speech inquiry to the care provider regarding the performance of the activity by the resident or regarding the care provider assistance that is given in the performance of the activity by the resident. If the resident did not require any touching, a path to dialog block 422 would be implemented.

At this stage, the self-performance and support information would indicate that the resident is pretty self-sufficient, and needs little physical support. In dialog block 422, an inquiry is made to the care provider regarding whether they provided non-physical support, such as whether they watched the resident or told the resident what to do. Separate paths through the speech dialog would then be chosen, depending upon the answer to that inquiry. If the care provider did not have to watch the resident or tell them what to do, it would be indicative that the resident is relatively self-sufficient and self-supporting such that they would be categorized as independent in the self-performance category of the ADL. After the inquiry of block 422, an inquiry is made regarding any kind of setup provided by the care provider, as illustrated by blocks 424 and 426. Depending upon the answers to those inquiries, the ADL category for support will either be none or that setup has been provided. Again, the ADL codes would be reflective of the particular speech dialog and the input speech from the care provider. Therefore, in accordance with one aspect of the invention, the speech input captured from the care provider that is responsive to the speech inquiries of the dialog, are used to determine a code that indicates the self-performance and the support information for a particular activity. The codes are then indicated as illustrated by blocks 428, 430, 432, and 434. For example, if the ADL code indicates 1, 0, it will be documented that, while the care provider watched or told the resident what to do, they did not have to provide any additional set up or support (block 432). An ADL code of 0, 0 would indicate that the resident is independent, and can handle the activity on their own with no assistance from the care provider. Other ADL codes are indicated in the various blocks of FIG. 9.

Returning to FIG. 6, depending upon the code determined through the ADL coding dialog, the self-performance and support information might be spoken back to the care provider as part of the dialog. For example, as illustrated in block 300, speech dialog may state or speak "Extensive, One-person" to indicate the ADL determination that was made pursuant to the speech dialog. Accordingly, the present invention provides an accurate indication of self-performance and support information even if the care provider or other person providing the documentation does not understand the ADL coding and the various categories. The present invention directs them through a suitable speech dialog, and based upon the speech dialog and the captured speech input from the care provider, makes the determination of the proper ADL codes that indicates the self-performance of the person and the support information associated with the ADL activity.

While the present invention has been illustrated by the description of the embodiments thereof, and while the embodiments have been described in considerable detail, it is not the intention of the application to restrict or in any way limit the scope of the appended claims to such detail. Additional advantages and modifications will readily appear to those skilled in the art. Therefore, the invention in its broader aspects is not limited to the specific details or representative apparatus and method, and illustrative examples shown and described. For example, the principles of the present invention may be adapted for a setting different than a nursing home. Accordingly, departures may be made from such details without departure from the spirit or scope of applicant's general inventive concept.

What is claimed is:

1. A method of assisting a care provider in the documentation of self-performance and support information for a person, the method comprising:

using at least one processor, providing a speech dialog with a care provider using the generation of speech to play to the care provider and the capture of speech spoken by a care provider, the speech dialog providing assistance to the care provider in providing care for a person according to a care plan for the person;

the care plan including at least one activity requiring a level of performance by the person;

for the at least one activity, providing at least one speech inquiry to the care provider, through the speech dialog, regarding performance of the activity by the person;

for the at least one activity, providing at least one speech inquiry to the care provider, through the speech dialog, regarding care provider assistance in the performance of the activity by the person;

capturing speech input from the care provider that is responsive to the speech inquiries; and determining, from the speech input, a code that indicates the self-performance of the person and support information for a care provider.

2. The method of claim 1, wherein the at least one speech inquiry to the care provider regarding performance of the activity by the person includes at least one inquiry regarding the level of participation of the person in the activity.

3. The method of claim 1, wherein the at least one speech inquiry to the care provider regarding care provider assistance in the performance of the activity by the person includes a speech inquiry regarding supporting the weight of a person during the activity.

4. The method of claim 1, wherein the at least one speech inquiry to the care provider regarding care provider assistance in the performance of the activity by the person includes a speech inquiry regarding the care provider touching the person during the activity.

5. The method of claim 1, wherein the at least one speech inquiry to the care provider regarding care provider assistance in the performance of the activity by the person includes a speech inquiry regarding the care provider setting up an item for the person.

6. The method of claim 1, wherein the at least one speech inquiry to the care provider regarding care provider assistance in the performance of the activity by the person includes a speech inquiry regarding the care provider watching the person or telling the person what to do.

7. The method of claim 1, wherein the at least one speech inquiry to the care provider regarding care provider assistance in the performance of the activity by the person includes a speech inquiry regarding the number of care providers participating in the activity.

8. The method of claim 1, further comprising:
providing multiple speech inquiries to the care provider, through the speech dialog, regarding care provider assistance in the performance of the activity by the person; and
varying a speech inquiry to a care provider based upon captured speech input that is responsive to a previous speech inquiry.

9. A system for assisting a care provider in the documentation of self-performance and support information for a person, the system comprising:
a portable computer having a processor and a memory;
a speaker operably coupled with the portable computer;
a microphone operably coupled with the portable computer; and
a program code resident in the memory and configured to be executed by the processor, the program code providing a speech dialog with a care provider using the generation of speech to a user played through the speaker and the capture of speech from a user using the microphone, the care plan including at least one activity requiring a level of performance by the person, the program code further configured to provide through the speech dialog, for the at least one activity, at least one speech inquiry to the care provider regarding performance of the activity by the person and at least one speech inquiry to the care provider regarding care provider assistance in the performance of the activity by the person and to capture speech input from the user that is responsive to the speech inquiries and determine a code that indicates the self-performance of the person and support information for a care provider.

10. The system of claim 9, wherein the at least one speech inquiry to the care provider regarding performance of the activity by the person includes at least one inquiry regarding the level of participation of the person in the activity.

11. The system of claim 9, wherein the at least one speech inquiry to the care provider regarding care provider assistance in the performance of the activity by the person includes a speech inquiry regarding supporting the weight of a person during the activity.

12. The system of claim 9, wherein the at least one speech inquiry to the care provider regarding care provider assistance in the performance of the activity by the person includes a speech inquiry regarding the care provider touching the person during the activity.

13. The system of claim 9, wherein the at least one speech inquiry to the care provider regarding care provider assistance in the performance of the activity by the person includes a speech inquiry regarding the care provider setting up an item for the person.

14. The system of claim 9, wherein the at least one speech inquiry to the care provider regarding care provider assistance in the performance of the activity by the person includes a speech inquiry regarding the care provider watching the person or telling the person what to do.

15. The system of claim 9, wherein the at least one speech inquiry to the care provider regarding care provider assistance in the performance of the activity by the person includes a speech inquiry regarding the number of care providers participating in the activity.

16. The system of claim 9, wherein the program code is further configured for providing multiple speech inquiries to the care provider, through the speech dialog, regarding care provider assistance in the performance of the activity by the person and varying a speech inquiry to a care provider based upon captured speech input that is responsive to a previous speech inquiry.

17. The system of claim 9 further comprising a headset, the headset including the speaker and microphone and being operably coupled with the portable computer.

\* \* \* \* \*